US011872157B2

(12) United States Patent
Enemark (10) Patent No.: US 11,872,157 B2
(45) Date of Patent: Jan. 16, 2024

(54) MICRO DROP ADAPTER FOR DROPPER BOTTLES

(71) Applicant: Nanodropper, Inc., Rochester, MN (US)

(72) Inventor: Paul Enemark, San Antonio, TX (US)

(73) Assignee: Nanodropper, Inc., Rochester, MN (US)

( * ) Notice: Subject to any disclaimer, the term of this patent is extended or adjusted under 35 U.S.C. 154(b) by 106 days.

(21) Appl. No.: 17/072,008

(22) Filed: Oct. 15, 2020

(65) Prior Publication Data

US 2021/0030589 A1 Feb. 4, 2021

Related U.S. Application Data (63) Continuation-in-part of application No. 15/950,300, filed on Apr. 11, 2018, now Pat. No. 10,932,947.
(Continued)

(51) Int. Cl.
| A61F 9/00 | (2006.01) |
| A61J 1/06 | (2006.01) |
| A61J 1/14 | (2023.01) |

(52) U.S. Cl.
CPC ............ *A61F 9/0008* (2013.01); *A61J 1/067* (2013.01); *A61J 1/1412* (2013.01)

(58) Field of Classification Search
CPC .... A61F 9/0008; A61F 9/0026; A61F 9/0009; A61F 9/00; A61F 2250/0069; A61J 1/067; A61J 1/1412; A61J 1/1418; A61J 1/1425; A61J 1/1481; A61J 1/1406; B65D 47/18; B65D 1/08; B65D 47/14; B65D 51/225; B65D 2251/0096; B65D 2401/00; B65D 2251/0025; B65D 25/48; B65D 47/2081;
(Continued)

(56) References Cited

U.S. PATENT DOCUMENTS

| 3,612,409 A | 10/1971 | Henning |
| 4,471,890 A | 9/1984 | Dougherty |

(Continued)

FOREIGN PATENT DOCUMENTS

| CN | 202236291 U | 5/2012 |
| CN | 104606048 A | 5/2015 |

(Continued)

OTHER PUBLICATIONS

Idropr, Internet web site, available at https://www.idropr.com/, date of publication unknown.
(Continued)

*Primary Examiner* — Nicholas J. Weiss
*Assistant Examiner* — Brandon W. Levy
(74) *Attorney, Agent, or Firm* — Westman, Champlin & Koehler, P.A.; Amanda M. Prose (57) ABSTRACT

A micro drop adapter that is adapted to engage with dropper bottles. The micro drop adapter engages with and surrounds the original tip of the bottle. The micro drop adapter comprises at least one inner tube that is urged against the original tip of the bottle forming a seal and a channel in fluid connection with the bottle. The micro drop adapter comprises an adapter tip that dispenses micro drops, which are drops having a volume of less than approximately 50 microliters. The micro drop adapter further comprises a cap.

8 Claims, 13 Drawing Sheets

Related U.S. Application Data (60) Provisional application No. 62/915,703, filed on Oct. 16, 2019.

(58) Field of Classification Search
CPC ............... B65D 1/0223; A61H 35/02; A61M 2210/0612; A61M 11/06; A61M 11/007; A61M 2210/0618; B01L 3/0272
See application file for complete search history.

(56) References Cited

U.S. PATENT DOCUMENTS

| | | | |
|---|---|---|---|
| 4,605,398 A | | 8/1986 | Herrick |
| 4,739,906 A | | 4/1988 | LoTurco |
| 5,221,027 A | | 6/1993 | Gibilsco |
| 5,226,568 A | | 7/1993 | Newton et al. |
| 5,261,572 A | * | 11/1993 | Strater ............... B01L 3/0282 |
| | | | 222/215 |
| 5,358,151 A | | 10/1994 | Strasenburgh |
| 5,373,972 A | | 12/1994 | Bystrom et al. |
| 5,611,788 A | | 3/1997 | Marchment |
| 6,105,828 A | | 8/2000 | Kanner et al. |
| 6,197,008 B1 | | 3/2001 | Hagele |
| 6,223,918 B1 | * | 5/2001 | Browne ............... B65D 51/18 |
| | | | 215/254 |
| 6,632,202 B1 | | 10/2003 | Hagele |
| 7,537,141 B1 | | 5/2009 | Robinson |
| 7,563,256 B2 | | 7/2009 | Hearne |
| 7,758,553 B2 | | 7/2010 | Poisson et al. |
| 7,846,140 B2 | | 12/2010 | Hagele |
| 8,216,195 B2 | | 7/2012 | Wu |
| 8,287,505 B2 | | 10/2012 | Pine |
| 8,517,222 B2 | | 8/2013 | Painchaud et al. |
| 10,932,947 B2 | * | 3/2021 | Enemark ............... B65D 47/18 |
| 2003/0024947 A1 | | 2/2003 | Joshi et al. |
| 2004/0074925 A1 | | 4/2004 | Faurie |
| 2006/0116649 A1 | | 6/2006 | Hagele |
| 2006/0191959 A1 | | 8/2006 | Davies et al. |
| 2007/0045354 A1 | * | 3/2007 | Boyd ............... B65D 1/08 |
| | | | 222/215 |
| 2007/0051362 A1 | | 3/2007 | Sullivan et al. |
| 2007/0102455 A1 | * | 5/2007 | Stark ............... A61M 11/08 |
| | | | 222/207 |
| 2007/0233020 A1 | * | 10/2007 | Hearne ............... B65D 47/18 |
| | | | 604/295 |
| 2009/0212133 A1 | | 8/2009 | Collins, Jr. |
| 2009/0259204 A1 | | 10/2009 | Galdeti et al. |
| 2009/0272769 A1 | | 11/2009 | Contreras et al. |
| 2013/0134186 A1 | | 5/2013 | Defemme et al. |
| 2015/0038925 A1 | | 2/2015 | Parunak et al. |
| 2016/0015957 A1 | * | 1/2016 | Tieck ............... A61J 1/1418 |
| | | | 604/533 |
| 2019/0224044 A1 | | 7/2019 | Song et al. |

FOREIGN PATENT DOCUMENTS

| | | |
|---|---|---|
| DK | 2986539 | 8/2018 |
| JP | H02106235 U | 8/1990 |
| JP | 07004812 | 2/1995 |
| JP | 2005211184 A | 8/2005 |
| KR | 101675989 B1 | 11/2016 |
| WO | 2014055676 A1 | 4/2014 |
| WO | 2014170736 A1 | 10/2014 |

OTHER PUBLICATIONS

Nanodropper, Internet web site, available at https://web.archive.org/web/20180630003914/https://nanodropper.com/, published on the Internet on Jun. 30, 2018.

Office Action issued for CN patent application Serial No. 201980037154.9, dated Jan. 28, 2022 with English machine translation.

* cited by examiner

MICRO DROP ADAPTER FOR DROPPER BOTTLES

CROSS-REFERENCE TO RELATED APPLICATIONS

This application claims the benefit of U.S. provisional patent application 62/915,703, filed Oct. 16, 2019. This application is also a continuation-in-part of U.S. nonprovisional patent application Ser. No. 15/950,300, filed Apr. 11, 2018.

DETAILED DESCRIPTION

An eye drop bottle typically dispenses about 50 microliters per drop, which is about twice the volume the eye can hold. As early as 1992, certain researchers advocated for the use of a "micro drop" in eye drop bottles. The proposed micro drop would consist of drop volumes of about 16 microliters, since the research indicated that the medicinal efficacy was not affected while patients experienced fewer side effects. For purposes of the present disclosure, a micro drop will be understood to be any drop having less than the typical 50 microliters volume. Additionally, it was found that patients preferred the micro drops. However, to date the use of micro drops has never been adopted by the pharmaceutical companies or bottle manufacturers. There may be various industry pressures or motivations preventing adoption of this technology by the manufacturers considering that if the drop is half the size, then the bottle will last twice as long, potentially resulting in sales volumes and profits being cut in half. However, that may not be true considering that shelf life limits extended or multiple uses of many medicinal drops. Therefore, production costs could be lowered for a company making smaller volume bottles without affecting sales.

Nevertheless, since current bottles do not make use of micro drops, there is a long felt patient need for a more efficient and comfortable drop applicator. Additionally, there are many non-medicinal use instances wherein consumers would find a micro-drop adapter advantageous. Take for example the daily cleaning and conditioning of contact lenses. Contact lens solution can be used more efficiently when dispensed in micro drops. The consumer benefits from the increased economy, and the public benefits from less run-off solution entering the water system.

To address this problem a dropper bottle could be manufactured with a micro-dropper tip. However, since that may or may not occur, consumers desire the option to change the bottle as it is sold or otherwise convert their existing legacy bottles into micro drop dispensing bottles. There have been prior art attempts to achieve this, but those have various failings. Take for example, U.S. Pat. No. 7,563,256 for a "Cannula Tip Eye Drop Dispenser" which sets out various dropper tips that are intended to replace or be substituted for the original tip that came with the bottle. In one embodiment, the replacement tip has a needle like portion that extends down into the bottle to penetrate the diaphragm barrier (the barrier is used to prevent contamination in certain medications). This is obviously not desirable because it damages and circumvents the purpose of the diaphragm barrier. Furthermore, the downward extending needle prevents the bottle from being completely drained, which defeats the purpose of the more efficient micro-drops. In another embodiment of the same patent, a replacement tip is provided that does not have a needle. However, both this replacement tip and the previously discussed tip pre-suppose that either the bottle had no existing dropper tip or the original tip of the bottle is removable. The modern reality is simply not so. Most liquids (including medicinal and non-medicinal) that are meant to be dispensed via drops are sold in a dropper bottle having a tip. And the tip of many modern-day dropper bottles is not removable because it is formed along with the bottle as a monolithic structure. Because of this, the prior art cannot be applied to the majority of dropper bottles consumers experience in the market.

It is a goal of the present invention to provide an adapter that will work with the majority of existing dropper bottles that a consumer will experience in the market of drop dispensable liquids. This adapter will convert a user's existing dropper bottle into a micro drop dispensing bottle. The present invention addresses the need in the form of an adapter that can be attached directly to the user's legacy or existing eye dropper bottle. To accomplish the goal of the present invention, the adapter comprises a coupler to attach to the original bottle, an internal sheath—referred to as the "inner tube"—configured to at least partially surround and make a seal with the tip of the original bottle, a micro drop forming tip that is in fluid connection with the inner tube, and a removable new cap that can engage the adapter to protect the micro drop forming tip and thereby protect the bottle contents from external contamination.

The micro drop adapter is described herein according to multiple implementations. As a convention for orientation, the descriptive directions of up, above, on top of, down, under, below, etc., may be used. One having ordinary skill in the art will understand that a bottle is typically oriented with the base or bottom of the bottle in the lowest position and the tip of the bottle will be positioned in the highest position. Therefore, terms such as up, above, on top of, etc., will refer to a relative position that is further from the base or bottom of the bottle. And similarly, terms such as down, under, below, etc., will refer to a relative position that is closer to the base or bottom of the bottle.

The typical prior art dropper bottle 100, shortened to "the bottle 100," is well understood in the art, but essentially consists of a circular or oval shaped base, a sidewall, and a top dispensing portion. See FIGS. 1-3. The bottle 100 is capable of dispensing drops having approximately 50 microliters in volume. The top dispensing portion of the bottle typically consists of an original drop dispensing tip 104 and a lid 105. See FIG. 2. The original drop dispensing tip 104, shortened to "original tip 104," is typically comprised of a substantially cylindrical threaded portion 106 below a substantially frustoconical cone 107 having a base that tapers to an opening 108 in fluid connection with inside of the bottle 100. The lid 105 engages the threaded portion 106 at the base of the original tip 104 to surround and enclose the original tip 104, thereby creating a seal against the opening 108. FIG. 3 shows a cross sectional view of the typical prior art eye dropper bottle 100 with the lid 105 removed.

The present disclosure describes various implementations of a micro drop adapter that is capable of dispensing micro drops. Some of the below described, implied, or understood implementations are capable of dispensing a micro drop of a particular pre-defined volume. However, certain implementations will dispense a micro drop having a pre-defined average volume in the range of 10-30 microliters.

Figure 1:
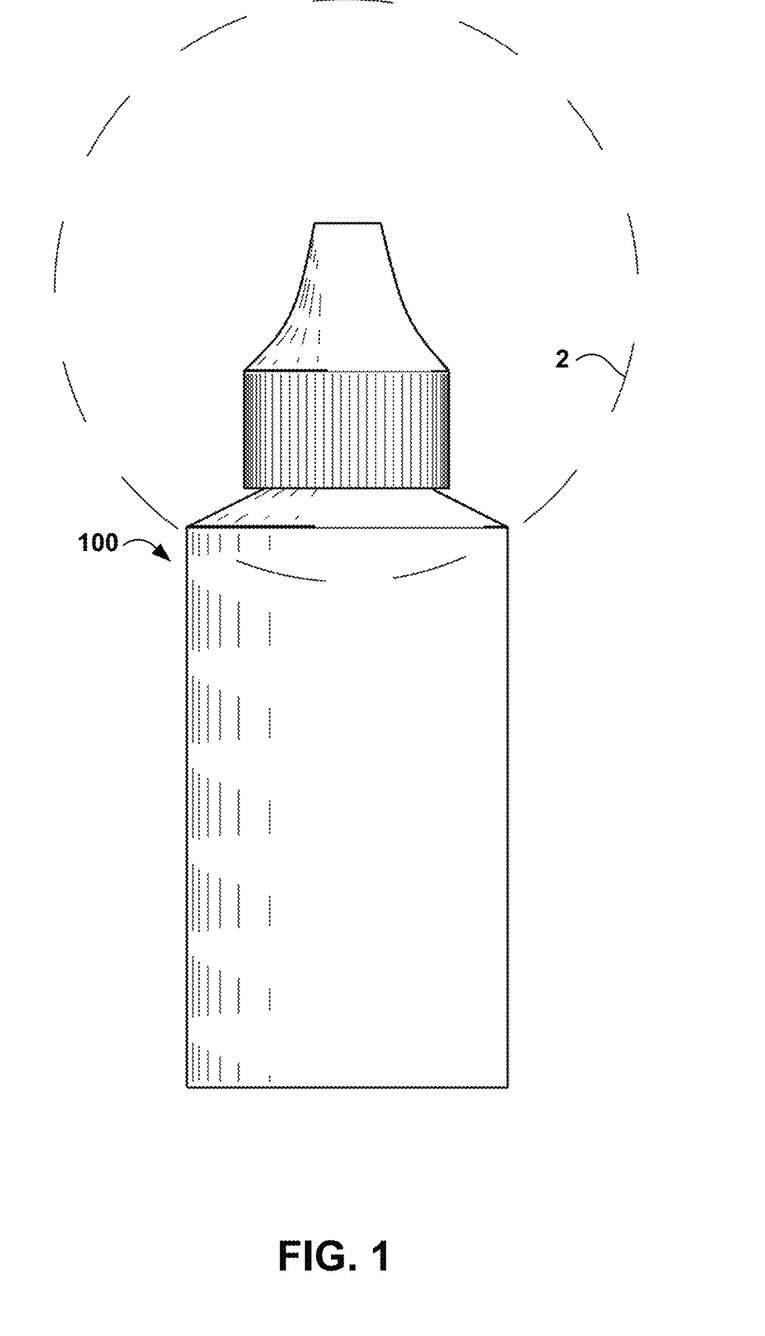
FIG. 1 shows an orthogonal front view of a typical prior art eye dropper bottle with the original lid secured in place.
Figure 2:
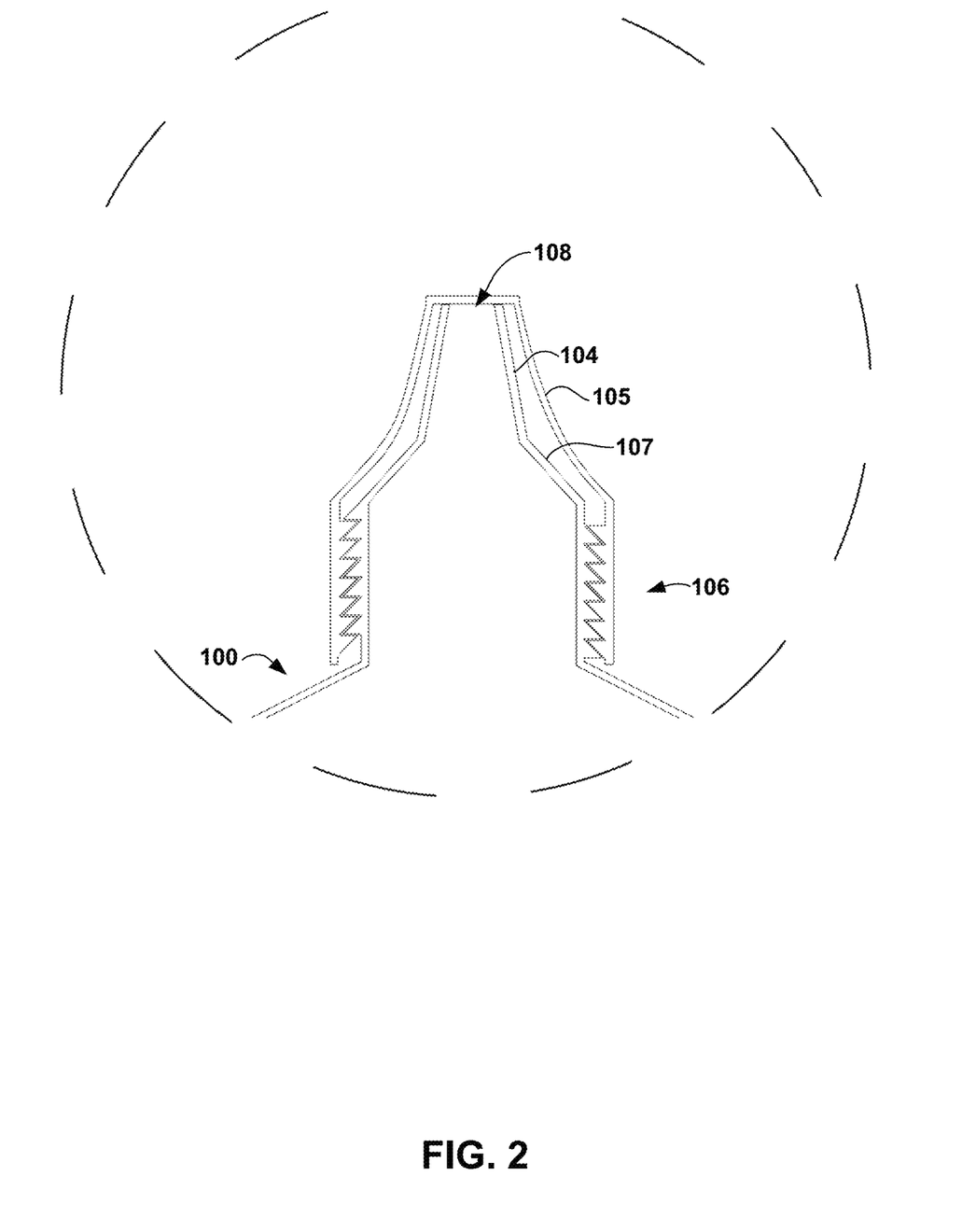
FIG. 2 shows a partial cross-sectional view of a typical prior art eye dropper bottle with the original lid secured in place through the section 2 of FIG. 1.
Figure 3:
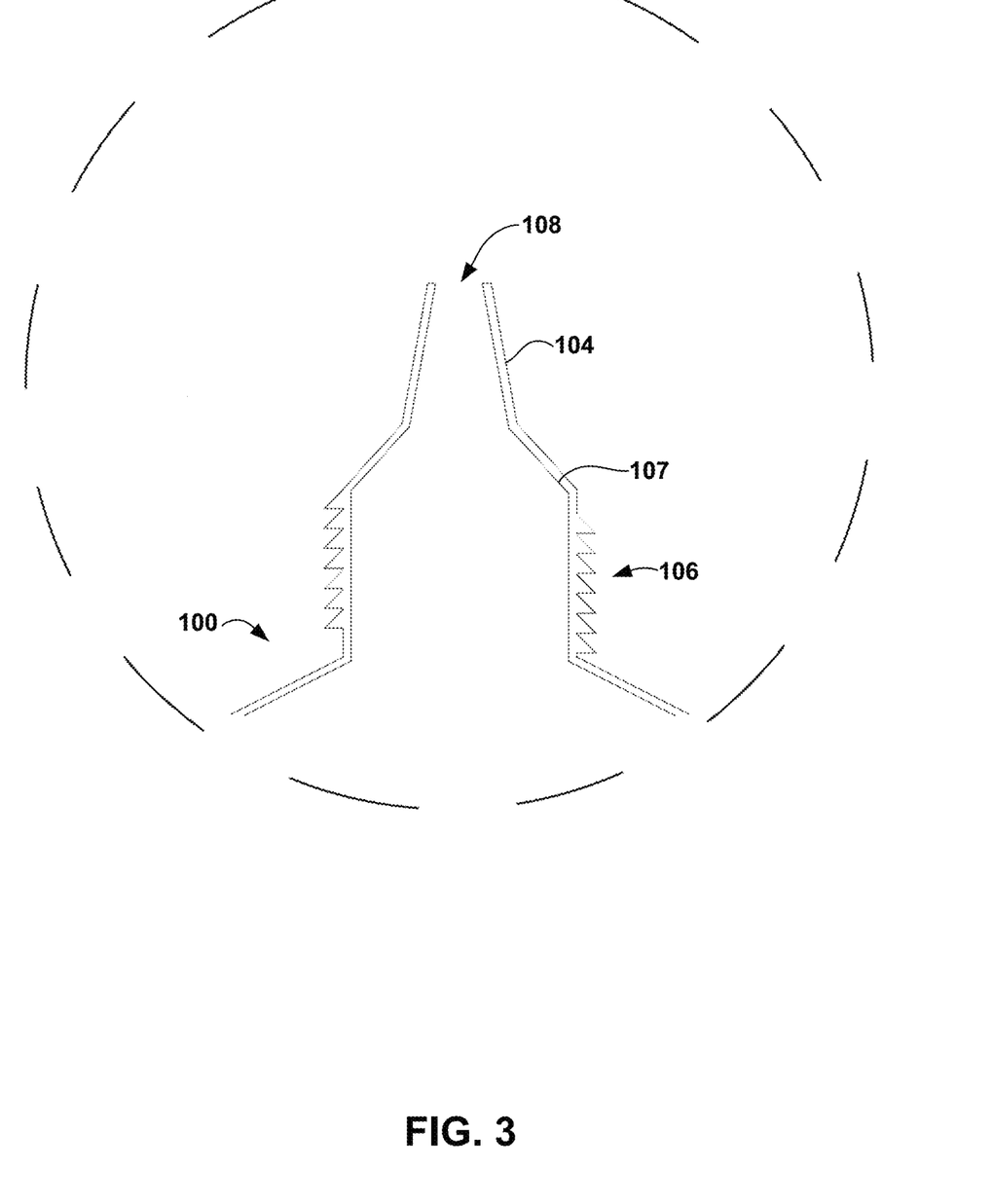
FIG. 3 shows the partial cross-sectional view of FIG. 2 illustrating the typical prior art eye dropper bottle of FIG. 1 with the original lid removed.
Figure 4:
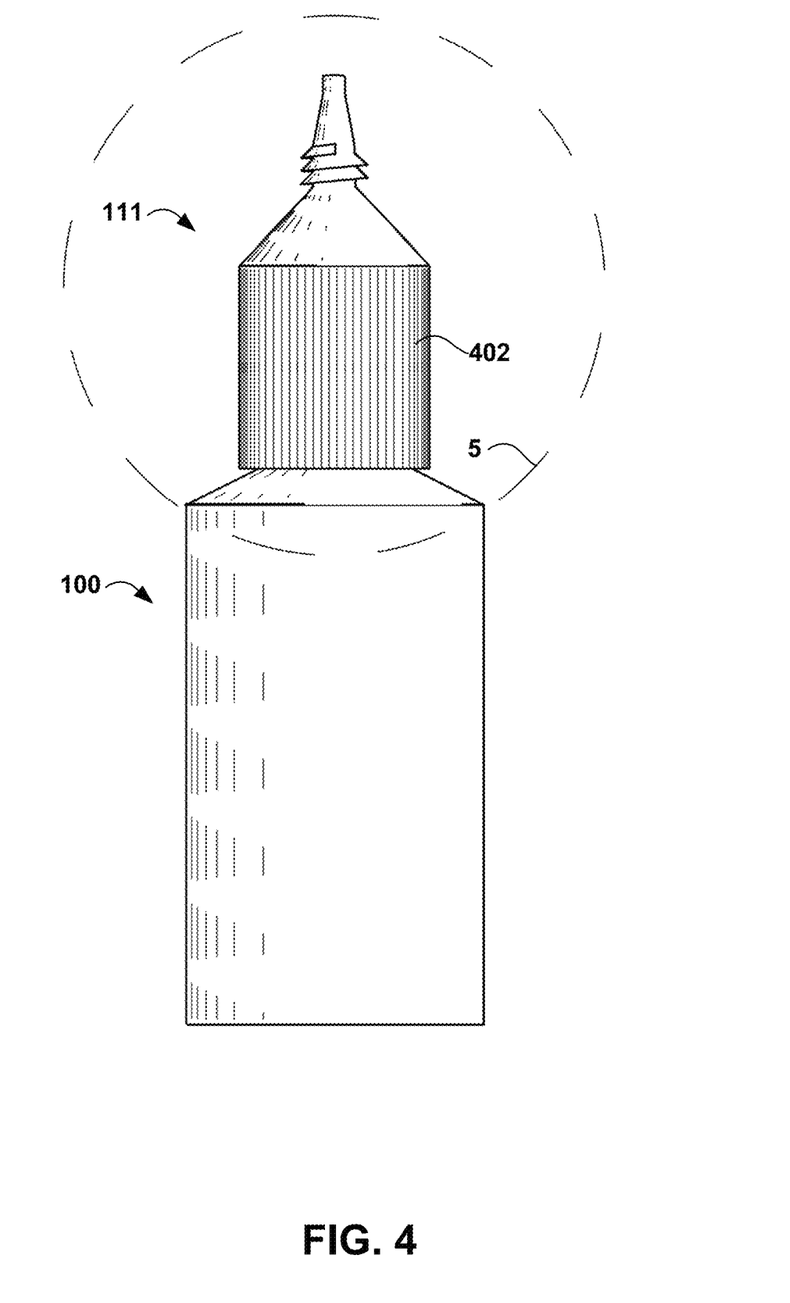
FIG. 4 shows an orthogonal front view of a first implementation of a micro drop adapter for dropper bottles of the present disclosure secured to the typical prior art eye dropper bottle.

The micro drop adapter 111, shortened to "the adapter 111," of the implementations of FIG. 4-7 is shown in orthogonal and cross-sectional views as positioned on the eye dropper bottle 100 of FIG. 1-3. The adapter 111 comprises a substantially cylindrical body section 112, a substantially frustoconical cone section 113, an inner tube 114, and an adapter tip section 115, such that the adapter tip section 115 is connected to the body section 112 via the cone section 113.

The body section 112 of the adapter 111 is tubular with a body outer wall 116, a body inner wall 117, a body top end 118, and a body bottom end 119, wherein the body bottom end 119 has a body opening 120 and the body top end 118 is connected to the widest portion of the cone section 113. The inner wall 117 of the body section 112 is configured to receive and engage the threaded portion 106 of the bottle 100 (see FIG. 2-3). Therefore, the body section 112 of the adapter 111 comprises a bottle retainer 121 positioned on the body inner wall 117 towards the body bottom end 119. In the implementation shown in FIG. 5, the bottle retainer 121 is comprised of a threaded section to engage with the threaded portion 106 of the bottle 100. Having read the present disclosure, it will be readily apparent to one having ordinary skill in the art that in addition to threads that correspond to the threads of the bottle, there are many other forms and mechanisms implementing the bottle retainer 121. For example, instead of threads, the bottle retainer 121 could utilize a multitude of fine filaments or bristles, or a deformable ring, or an elastically deformable ring—such that the threaded portion 106 of many different bottles 100 could be engaged without prior knowledge of the particular thread dimensions. In some implementations, the body section further comprises a grip enhancer 402 on the exterior surface. In some implementations the grip enhancer is a multitude of grooves formed into the body outer wall.

Figure 5:
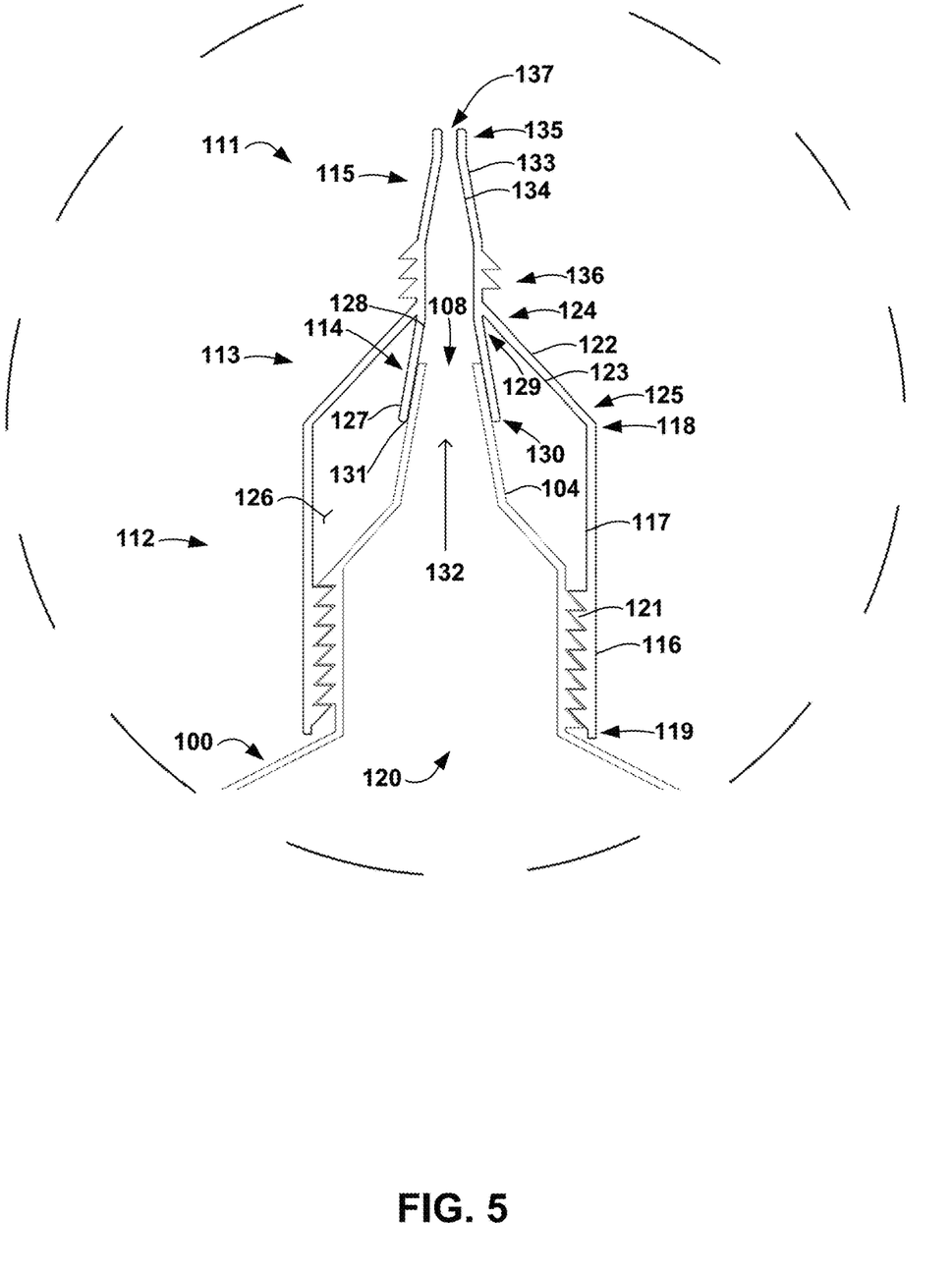
FIG. 5 shows a partial cross-sectional view of the micro drop adapter of FIG. 4 secured to the typical prior art eye dropper bottle through the section 5 of FIG. 4.
Figure 6:
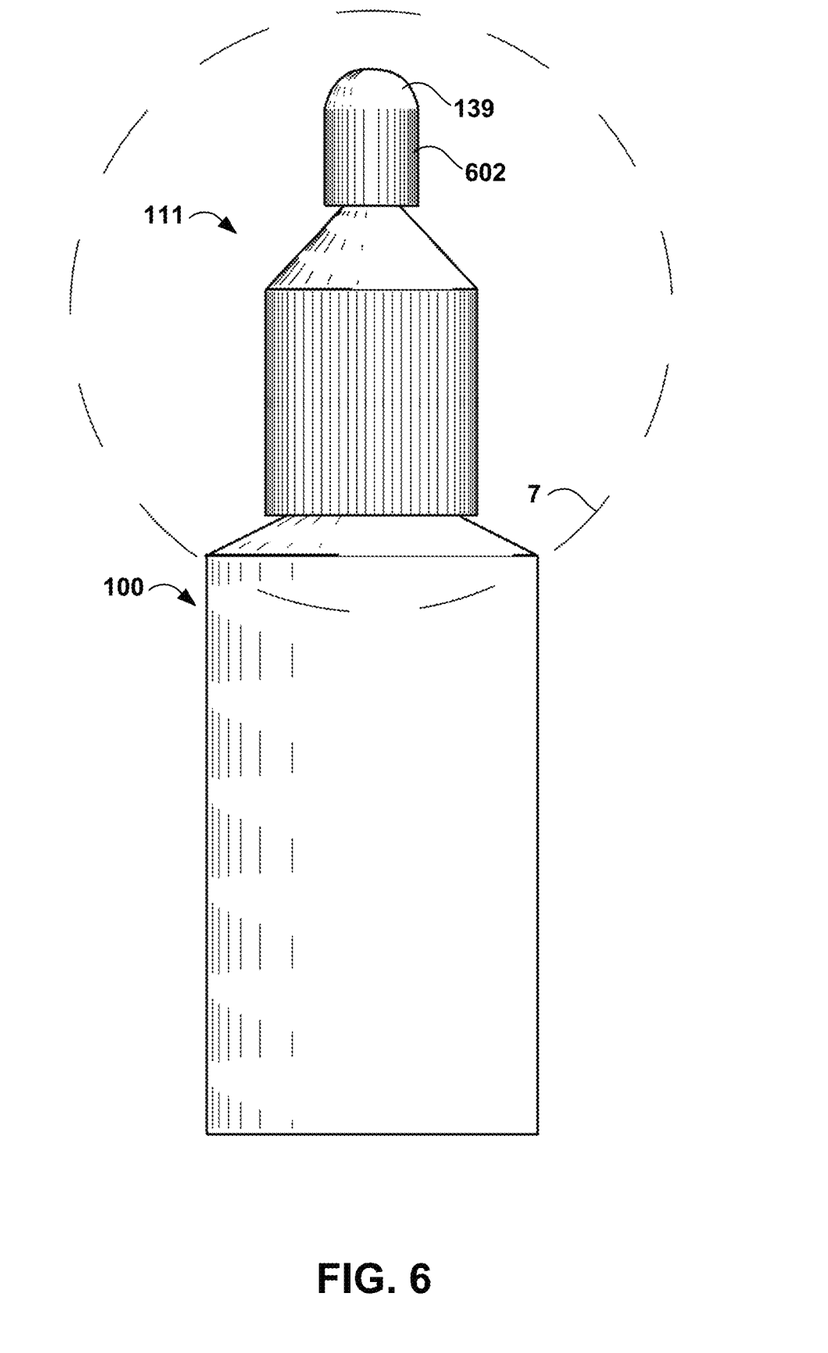
FIG. 6 shows an orthogonal front view of a second implementation of a micro drop adapter for dropper bottles of the present disclosure secured to the typical prior art eye dropper bottle.

The substantially frustoconical cone section 113, or simply the "cone section 113," of the adapter 111 has a cone outer wall 122, a cone inner wall 123, a cone top end 124, and a cone bottom end 125. The cone bottom end 125 is connected to the body top end 118. The cone inner wall 123 of the cone section 113 and the body inner wall 117 of the body section 112 together define a cavity 126. The cavity 126 is capable of accommodating a diverse range of original tip 104 shapes.

In some implementations, the micro drop adapter does not have a cone section 113 but rather the body section 112 creates the cavity 126 with the adapter tip section 115.

Still referring to FIG. 5, the inner tube 114 comprises an inner tube outer wall 127, an inner tube inner wall 128, an inner tube top end 129, and an inner tube bottom end 130. The inner tube top end 129 is connected to the cone inner wall 123 at the cone top end 124. The inner tube 114 extends downward from the cone top end 124 into the cavity 126. The inner tube bottom end 130 is adapted to contact the original tip 104 of bottle 100 such that at least part of the inner tube inner wall 128 forms a seal 131 against the exterior of original tip 104 of bottle 100 without obstructing opening 108 of bottle 100. Thus, inner tube inner wall 128 forms a channel 132 in fluid connection with opening 108 of bottle 100 and its contents.

In some implementations, inner tube 114 is a cylindrical tube. In other implementations, inner tube 114 is a frustoconical tube. In some implementations, inner tube 114 is made of a material that is at least partially elastically deformable. In some implementations, inner tube 114 is made of one or more of the materials comprising the following group: rubber, rubberized silicone, silicone, and plastic.

Still referring to FIG. 5, the adapter tip section 115 comprises a tip section outer wall 133, a tip section inner wall 134, a tip section top end 135, a tip section bottom end 136, and an adapter tip opening 137. The tip section bottom end 136 is connected to the cone top end 124 and the inner tube top end 129, such that the tip section inner wall 134 continues channel 132 and is in fluid connection with the bottle 100. The adapter tip section 115 extends upward from the cone top end 124. Adapter tip opening 137 is positioned at the tip section top end 135. The adapter tip section 115 is configured to dispense individual micro drops from adapter tip opening 137.

In some implementations, adapter tip section 115 will comprise a narrow tube of cylindrical shape. In other implementations, adapter tip section 115 will comprise a tapered tube shape. Regardless of shape or dimension, the adapter tip section 115 is adapted to form and dispense micro drops.

Figure 7:
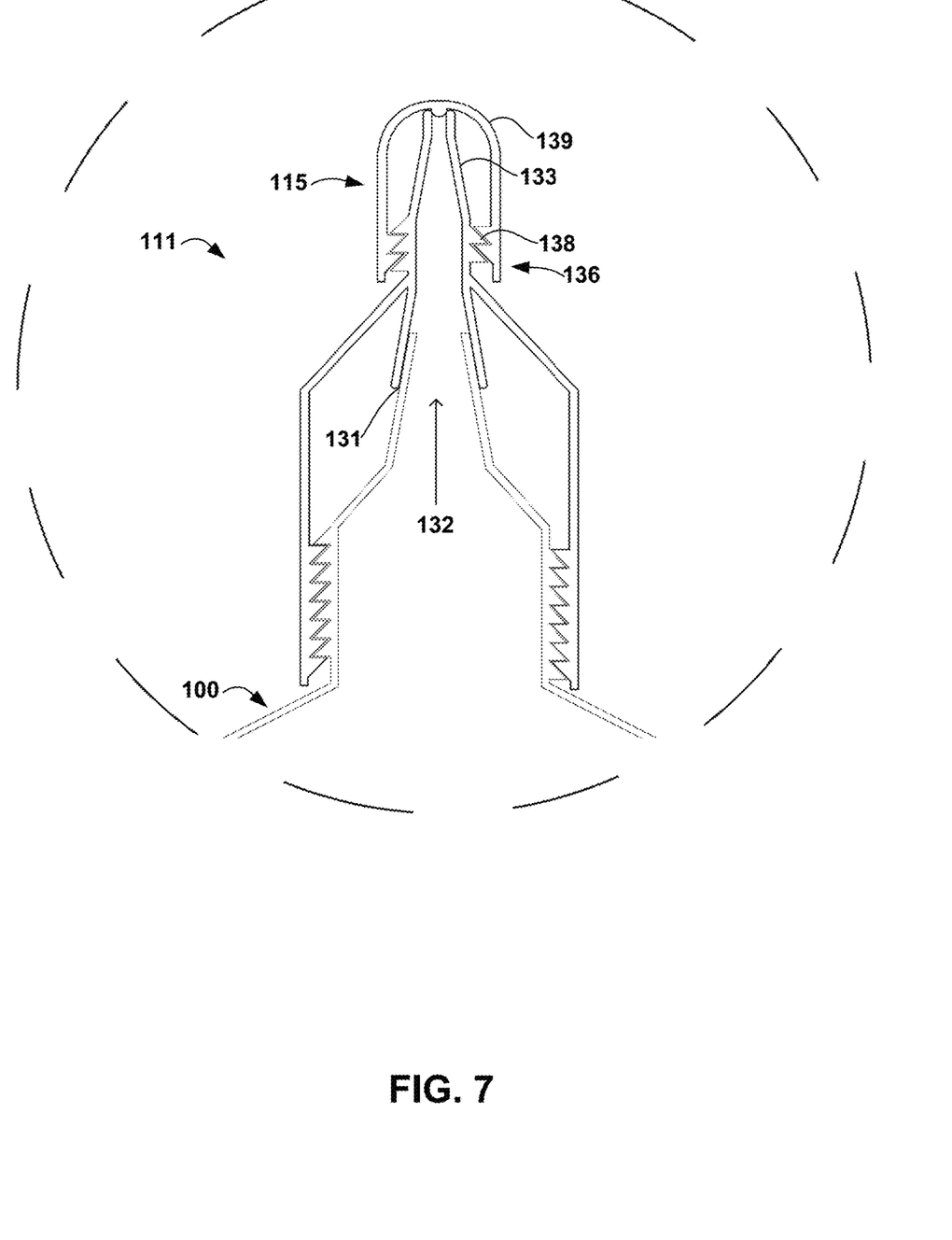
FIG. 7 shows a partial cross-sectional view of the micro drop adapter of FIG. 6 secured to the typical prior art eye dropper bottle through the section 7 of FIG. 6.
Figure 8:
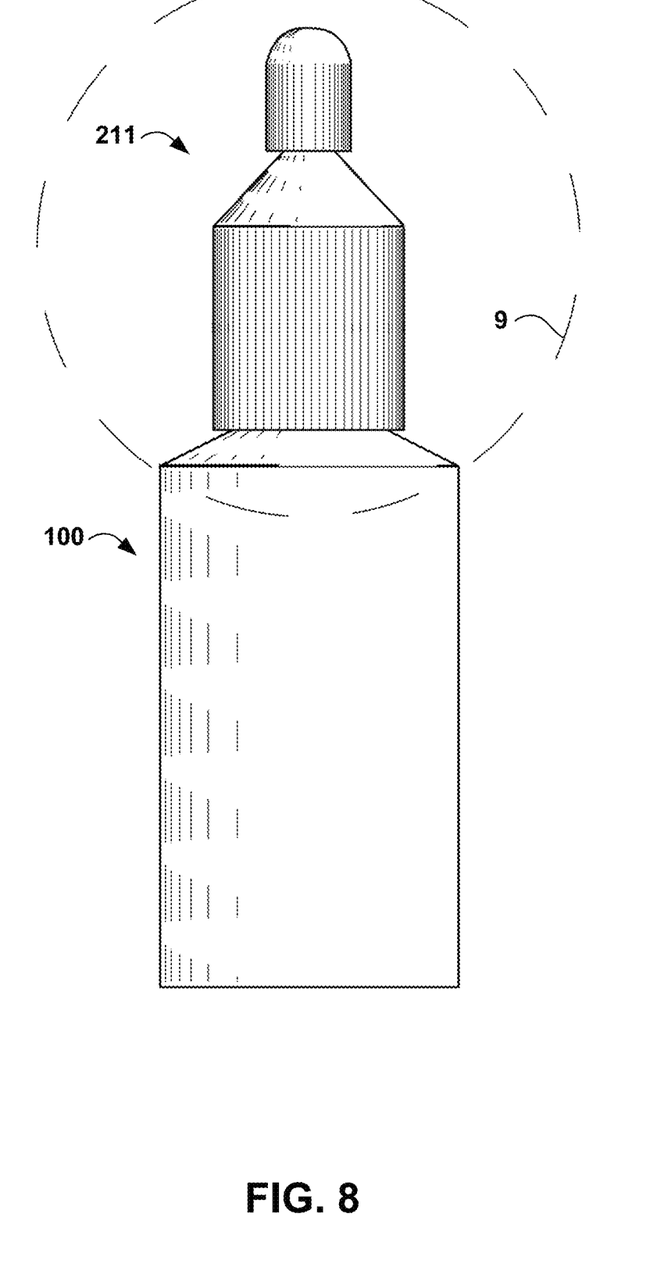
FIG. 8 shows an orthogonal front view of a third implementation of a micro drop adapter for dropper bottles of the present disclosure secured to the typical prior art eye dropper bottle.

Some implementations will further comprise a cap for the adapter to close off the dispensing channel. Adapter cap 139 (see, e.g., FIG. 7) will close channel 132 when fully engaged with adapter tip section 115, thus preventing the contents of bottle 100 from being unintentionally dispensed. Referring to the implementation seen in FIG. 7, the tip section outer wall 133 will have a cap retainer 138 positioned towards tip section bottom end 136. The cap retainer 138 will engage adapter cap 139. In FIGS. 5 and 7, the cap retainer 138 is depicted as a threaded section that is engages with the corresponding threaded section of adapter cap 139. However, having read the present disclosure it will be readily apparent to one having ordinary skill in the art that in addition to threads that correspond to the threads of the adapter cap 139, there are many other forms and mechanisms the cap retainer 138 could be comprised of such as a simple lip and groove that retains the adapter cap 139 via an inwardly directed compressive force. Moreover, having read the present disclosure it will be readily apparent to one having ordinary skill in the art that cap retainer 138 could be positioned on the cone section 113 or body section 112 in alternative implementations. In some implementations, the adapter cap further comprises a grip enhancer 602 on the exterior surface. In some implementations the grip enhancer is a multitude of grooves formed into the cap adapter outer wall.

Figure 9:
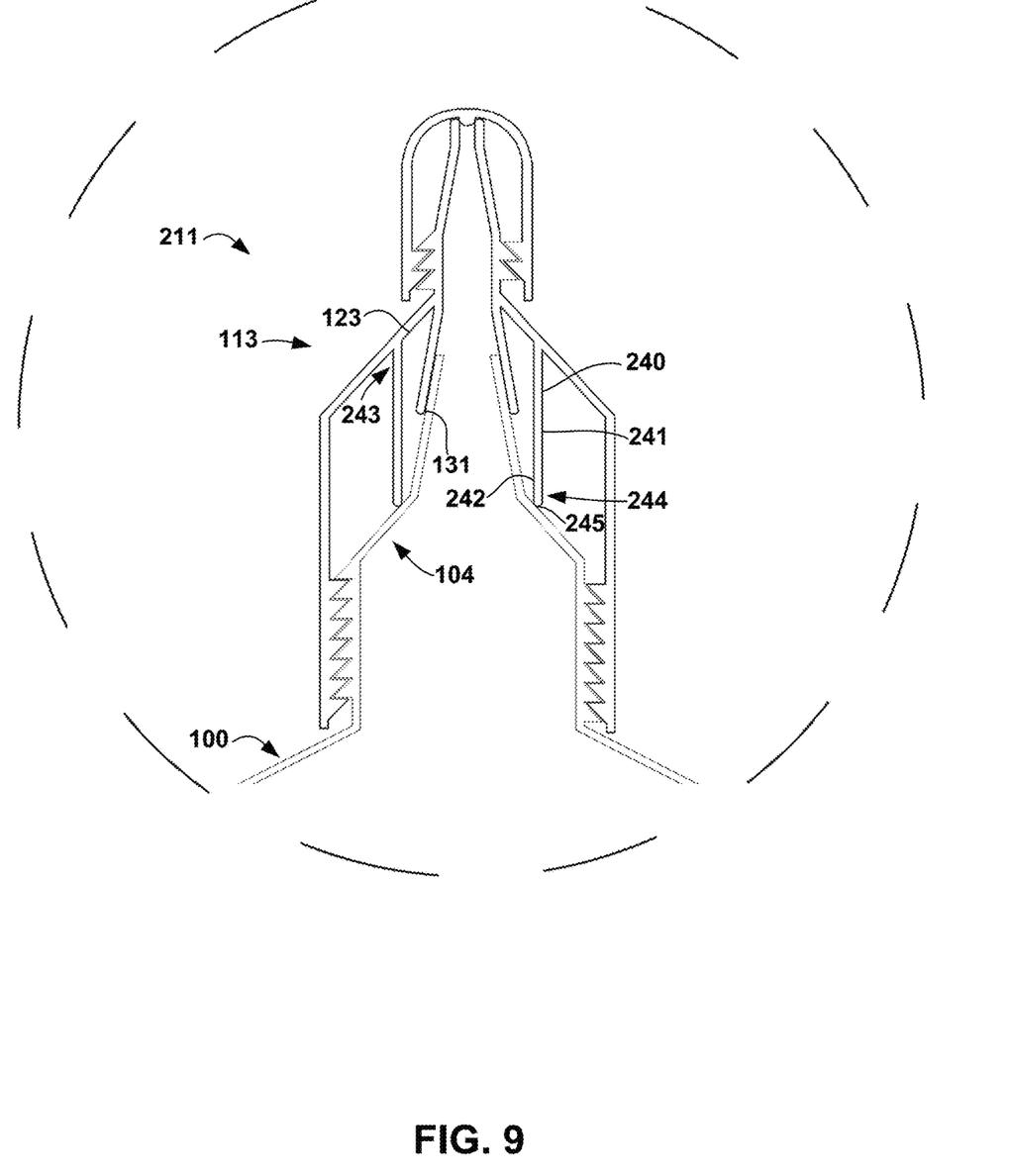
FIG. 9 shows a partial cross-sectional view of the micro drop adapter of FIG. 8 secured to the typical prior art eye dropper bottle through the section 9 of FIG. 8.

Turning now to FIG. 9 for reference, some implementations further comprise at least a second inner tube. Adapter 211, shown in FIG. 9, is similar to adapter 111 in many respects. Indeed, adapter 211 comprises all of the features and described elements of adapter 111 unless otherwise specified. However, adapter 211 further comprises a second inner tube 240. Second inner tube 240 comprises a second inner tube outer wall 241, a second inner tube inner wall 242, a second inner tube top end 243, and a second inner tube bottom end 244. The purpose of the second inner tube 240 is to create a second seal 245. Second inner tube top end 243 is connected to the cone inner wall 123. The second inner tube 240 extends down into cavity 126 such that the second inner tube bottom end 244 contacts the exterior of original tip 104. The second seal 245 is created at the point of contact between bottom end 244 and original tip 104. As with the inner tube 114, second inner tube 240 is comprised of rigid materials of construction in some implementations and flexible—resiliently deformable—materials of construction in other implementations.

The adapter 211 seen in FIG. 9 features a second inner tube 240. However, having read the present disclosure it will be understood by one having ordinary skill in the art that an alternative implementation of the presently disclosed adapter could be described as comprising at least one inner tube that creates at least one seal. In other words, some embodiments will feature a multitude of inner tubes creating a multitude of seals. The additional seals may be desired in certain adapter implementations for a variety of reasons such as greater resistance to leaking under the applied pressure while dispensing drops, or simply for the purpose of accommodating a larger range of bottle 100 original tip 104 shapes and sizes. The second inner tube 240 of the adapter 211 is also depicted in FIG. 9 as having a larger diameter but being concentric with inner tube 114. This is true in some implementations but one having ordinary skill in the art will appreciate upon reading the present disclosure that this is not a limitation that will apply to all implementations of the present invention.

The adapter implementations have been described as connected sections and functional parts (such as a body section, a cone section, an inner tube section, etc.). That is strictly true of certain implementations. However, having read the present disclosure it will be understood by one having ordinary skill in the art that some implementations will be formed monolithically such that the sections and functional elements are not separate parts that have been connected after the fact—but rather are elements forming a whole unit. In fact, FIGS. 5, 7, and 9 show such implementations.

The adapter of some implementations is constructed from a material that is suitable for sterilization procedures. Some sterilization procedures utilize intense ultraviolet light; therefore, a suitable material of construction will have the property of being undamaged or highly resilient to exposure to intense ultraviolet light. In plastics, the term is "UV stabilized." Another common sterilization procedure is the use of an autoclave, which involves high pressure and heat. Therefore, other implementations will be constructed of a material that can withstand the pressure and heat of autoclave sterilization.

Figure 10:
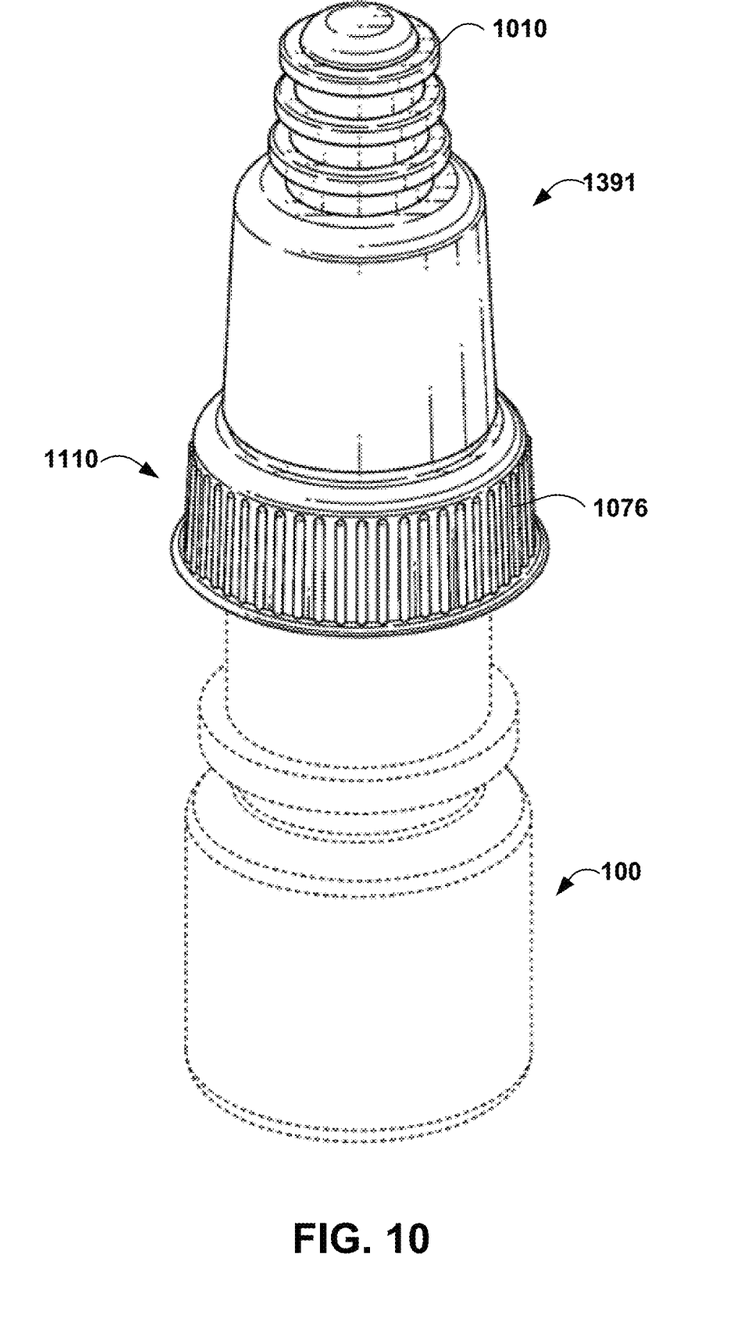
FIG. 10 shows a perspective view of a micro drop adapter secured to an eye dropper bottle according to another implementation of the present disclosure.

FIG. 10 shows a perspective view of a micro drop adapter secured to an eye dropper bottle according to another implementation of the present disclosure. FIG. 10 shows adapter 1110 secured to eye dropper bottle 100 (shown in dotted lines). Cap 1391 is shown connected to adapter 1110. Cap 1391 connects to adapter 1110 with a snap fit. The upper portion of cap 1391 comprises at least one ring 1010 (a grip enhancer) of material that assists a user in gripping and pulling cap away from adapter 1110 to expose the micro drop tip. As shown in FIG. 10, three rings 1010 are shown on cap 1391. Adapter 1110 is also shown comprising ridges 1076 (another grip enhancer) that surround the base of adapter 1110 to assist in gripping adapter 1110 when threading adapter 1110 onto and off of eye dropper bottle 100 and uncoupling cap 1391 from adapter 1110.

Figure 11:
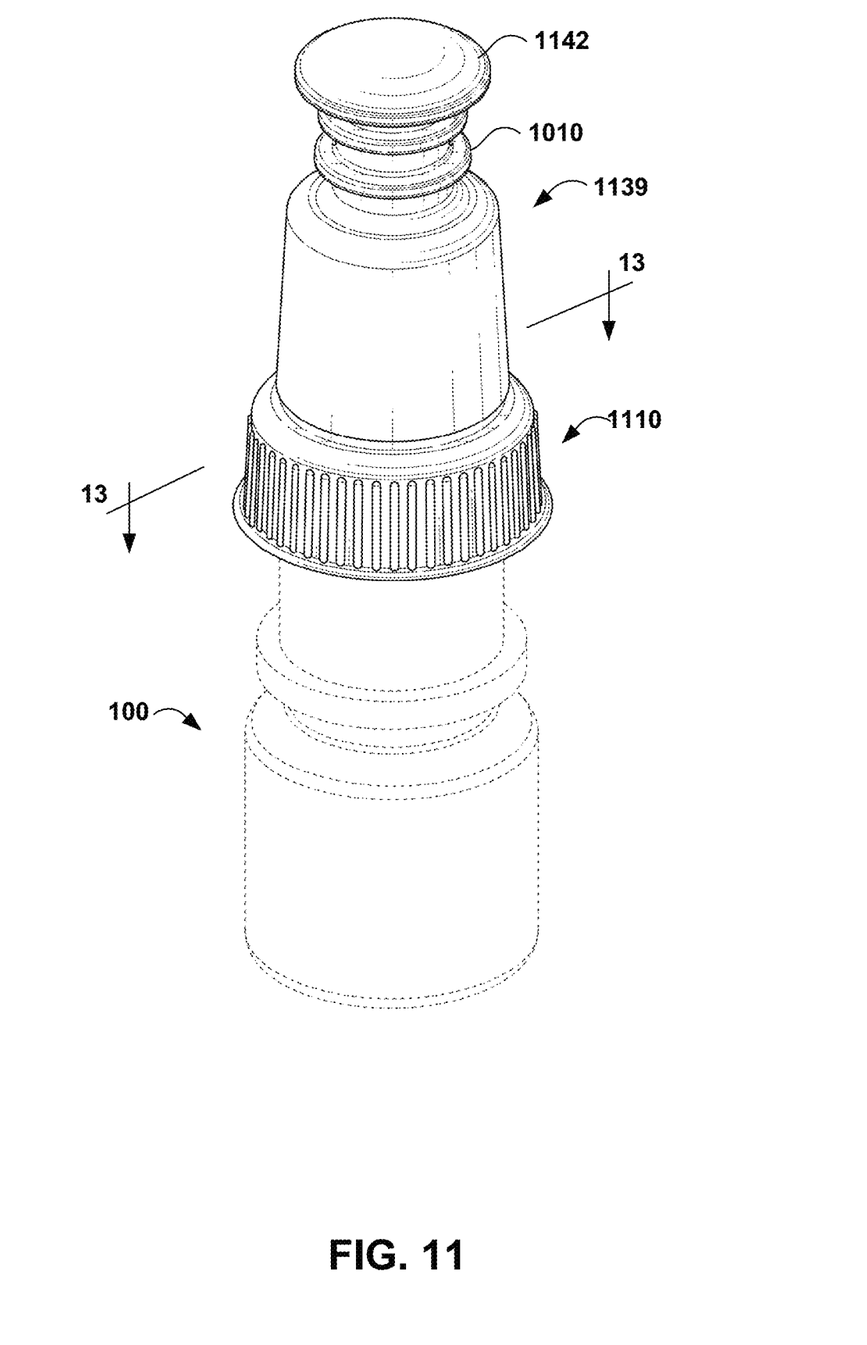
FIG. 11 shows a perspective view of a micro drop adapter secured to an eye dropper bottle according to yet another implementation of the present disclosure.

FIG. 11 shows a perspective view of a micro drop adapter secured to an eye dropper bottle according to yet another implementation of the present disclosure. The implementation shown in FIG. 11 is substantially similar to the implementation shown in FIG. 10 except for cap 1139. Cap 1139 has an additional upper disc-shaped element 1142 (a grip enhancer) that provides additional leverage for a user when decoupling cap 1139 from adapter 1110. Cap 1139 is also shown with two of ring 1010 positioned beneath upper disc-shaped element 1142. Thus, the cap 1139 comprises two different types of grip enhancers, a first grip enhancer (upper disc-shaped element 1142) and a second grip enhancer (ring 1010).

Figure 12:
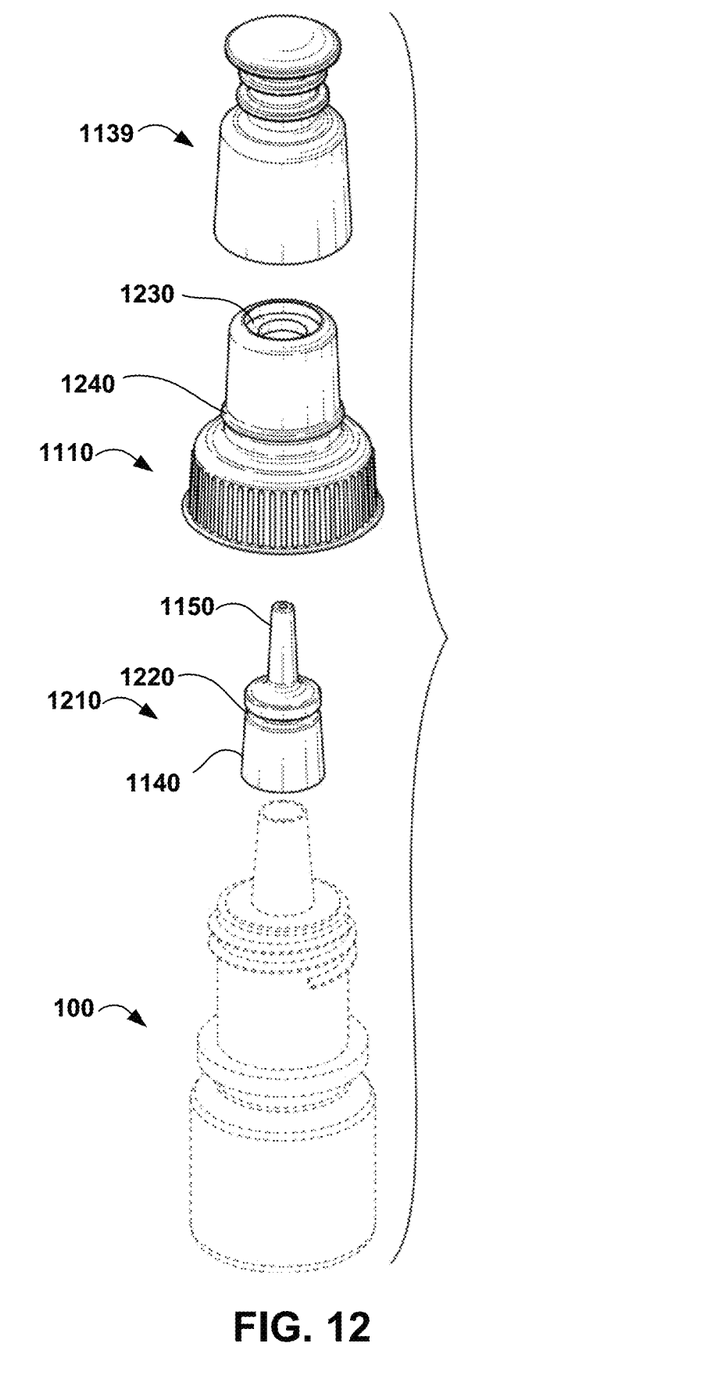
FIG. 12 shows an exploded perspective view of the micro drop adapter of FIG. 11.

FIG. 12 shows an exploded perspective view of the micro drop adapter of FIG. 11. Internal element 1210 comprises inner tube 1140 and an adapter tip section 1150. Internal element 1210 comprises a circumferential groove 1220 that interfaces with a corresponding circumferential ring 1230 in adapter 1110. Adapter tip section 1150 is flexible. Adapter 1110 has an annular ring 1240 that assists in securing cap 1139 to adapter 1110.

Figure 13:
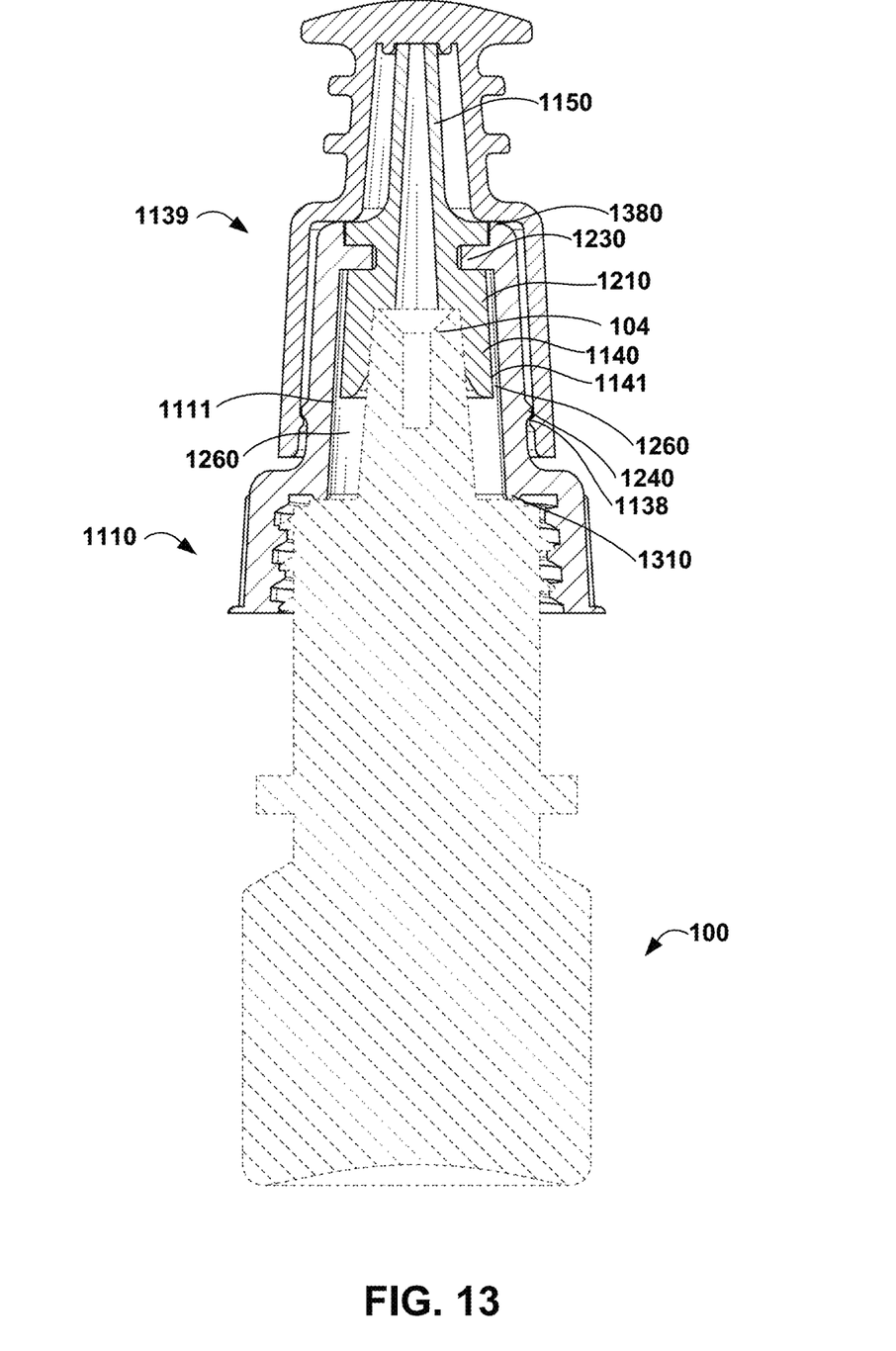
FIG. 13 shows a sectional view through the section 13-13 of FIG. 11.

FIG. 13 shows a sectional view through the section 13-13 of FIG. 11. Internal element 1210 (a secondary tip) is connected to adapter 1110 by way of circumferential groove 1220 and the corresponding circumferential ring 1230 in adapter 1110. In FIG. 13, circumferential ring 1230 is shown filling circumferential groove 1220 (circumferential groove 1220 is not labeled in FIG. 13, see FIG. 12 which shows circumferential groove 1220). This interaction captures internal element 1210 within adapter 1110. This is advantageous at least for the reason that it assists in seating inner tube 1140 onto original drop dispensing tip 104 as adapter 1110 is threaded onto eye dropper bottle 100. A tight seal is formed between original drop dispensing tip 104 and inner tube 1140 when adapter 1110 is properly secured on eye dropper bottle 100. As similarly described in an implementation of the present disclosure above, cavity 1260 is formed between outer wall 1141 of inner tube 1140 and the inner wall 1111 of adapter 1110. Regarding internal element 1210, it is noted that adapter tip section 1150 extends above the upper surface 1380 of adapter 1110 and an inner tube section 1140 extends below the upper surface 1380 of the adapter 1110. Cavity 1260 is enclosed by inner wall 1111 of the adapter 1110. Cavity 1260 surrounds inner tube 1140. Cavity 1260 provides space for inner tube 1140 to flex so as to accommodate original drop dispensing tip of different sizes as well as dropper bottles of differing dimensions, including those with different thread numbers and heights.

FIG. 13 also shows the interaction of annular ring 1240 with a corresponding annular ring 1138 on cap 1139 (such structure embodying a cap retainer). An annular crush ring 1310 is also present on adapter 1110 as shown. The annular crush ring 1310 assists seating adapter 1110 onto the upper dropper bottle, as shown.

The implementation of FIG. 10-13 reduces the volume of fluid ejected from adapter tip section 1150 to a micro drop volume as described above. The adapter tip section 1150 forms a secondary tip (secondary to the original drop dispensing tip 104) for attaching to a container (eye dropper bottle 100) and is configured to reduce a volume of a droplet of fluid ejected from the container. The volume of the droplet ejected from the container is reduced on a microliter scale as the assembly is configured to reduce the volume of the droplet ejected per squeeze to a micro drop volume. As shown in FIG. 13, cap 1139 caps the opening of adapter tip section 1150.

Although the invention has been described and illustrated with a certain degree of detail or with reference to one or more particular implementations, it is understood that the present disclosure has been made only by way of example. It should be understood that the invention is not intended to be limited to the particular forms disclosed. Furthermore, the invention is amenable to various modifications and alternative forms. Obvious variations and other various changes in the composition, combination, and arrangement of parts can be utilized to by those skilled in the art without departing from the spirit and scope of the invention, as herein disclosed and claimed.

What is claimed is:

1. A micro drop adapter assembly for a container having an original dispensing tip, the micro drop adapter assembly comprising:
    an internal secondary tip comprising:
        an opening configured to surround a terminal length of the original dispensing tip of the container for connecting the secondary tip to the original dispensing tip;
        a circumferential groove on a base thereof; and
        an inner tube that extends downwardly without penetrating an opening of the original dispensing tip,
        wherein the secondary tip is monolithically formed from a flexible material
    wherein the inner tube is a frustoconical tube that fits around a circumference of the original dispensing tip and forms a seal against an exterior surface of the original dispensing tip without obstructing the opening of the original dispensing tip;
    an adapter configured to threadably connect to the container for securing the secondary tip between the adapter and the container,
    wherein the adapter comprises a circumferential ring that corresponds to and couples to the circumferential groove on the base of the secondary tip, thereby connecting the adapter to the secondary tip and forming a cavity defined by an outer wall of the inner tube and an inner wall of the adapter,
    wherein the assembly is removably securable to the container without removal of the original dispensing tip,
    wherein the container is a squeeze type container,
    wherein the secondary tip is configured to reduce a volume of a droplet of fluid ejected from the original dispensing tip of the container wherein the original dispensing tip of the container is not removed or altered when the assembly is installed on the container, and
    wherein the volume of the droplet ejected from the container is reduced on a microliter scale.

2. The micro drop adapter of claim 1, the assembly comprising a cap to cap the secondary tip when the cap is connected to the adapter.

3. The micro drop adapter of claim 2 further comprising a cap retainer to retain the cap on the adapter.

4. The micro drop adapter of claim 2, the cap comprising at least one grip enhancer to assist removal of the cap.

5. The micro drop adapter of claim 2, the cap comprising at least one type of grip enhancer to assist removing the cap from the adapter.

6. The micro drop adapter of claim 2, the cap comprising at least two types of grip enhancers to assist removing the cap from the adapter.

7. The micro drop adapter of claim 1, the adapter comprising a threaded section that corresponds to a threaded section on the container.

8. The micro drop adapter of claim 7, the adapter comprising a grip enhancer comprising a multitude of grooves.

* * * * *